| United States Patent [19] | [11] Patent Number: | 4,808,535 |
|---|---|---|
| Isbister | [45] Date of Patent: | Feb. 28, 1989 |

[54] ACINETOBACTER SPECIES AND ITS USE IN REMOVING ORGANIC SULFUR COMPOUNDS

[75] Inventor: Jenefir D. Isbister, Potomac, Md.

[73] Assignee: Atlantic Research Corporation, Alexandria, Va.

[21] Appl. No.: 893,231

[22] Filed: Aug. 5, 1986

[51] Int. Cl.[4] .................... C12N 1/20; C10G 32/00
[52] U.S. Cl. .................... 435/252.1; 435/262; 435/282
[58] Field of Search .................... 435/253, 262, 282

[56] References Cited

U.S. PATENT DOCUMENTS 4,562,156  12/1985  Isbister et al. .................... 435/253
4,632,906  12/1986  Kopacz .................... 435/282
4,659,670   4/1987  Stevens, Jr. et al. .................... 435/262

OTHER PUBLICATIONS

ATCC Catalogue of Strains 15th edition 1982, pp. 59–62.

*Primary Examiner*—Thomas G. Wiseman
*Assistant Examiner*—Charles L. Patterson, Jr.
*Attorney, Agent, or Firm*—Frank P. Presta

[57] ABSTRACT

A novel mutant microorganism Acinetobacter species CB2 having a registry number ATCC #53515 has been produced by chemical mutagenesis and is effective in removing organic sulfur compounds from carbonaceous materials such as fossil fuels e.g., coal, petroleum and petroleum products.

5 Claims, No Drawings

ACINETOBACTER SPECIES AND ITS USE IN REMOVING ORGANIC SULFUR COMPOUNDS

BACKGROUND

Most coals and petroleum contain large quantities of sulfur which form corrosive air and water pollutant products during combusion. Chemical and physical processes have been developed and are capable of removing inorganic sulfur contaminants such as sulfates and iron pyrites. A number of chemical processes for removal or organic sulfur are under investigation. Some of the processes being evaluated on a laboratory or pilot scale are oxydesulfurization, chlorinolysis, oxidation, hydrodesulfurization and gravimelt. According to Berry, (Berry, R. I. (1981)), "Guide to Coal Cleaning Methods," Chemical Engineering, Jan. 26, projected total product costs from bench and pilot scale operations ranged from $41 to $58 per ton (in 1979 U.S. dollars) for 10 to 50% organic sulfur removal.

Microbial treatment for removal of organic sulfur from coal may have important advantages. High temperatures, high pressures and corrosion resistant equipment are required for the chemical processes currently being evaluated. Microbial processes do not require high temperatures, high pressure or corrosion resistant equipment and, generally, inexpensive construction materials can be used resulting in low capital costs. Processing costs can also be low if waste materials and or inexpensive nutrient sources are used to support microbial growth. Ambient conditions may be used for biological treatment in many locales. In addition, microbial treatment will probably not significantly alter the coal structure or composition except for the sulfur removal, and will not substantially reduce the caloric content of the coal.

Experimental investigations for microbial treatment of petroleum and coal have used a variety of microorganisms, including genera such as Pseudomonas, Alcaligenes, Bacillus, Desulfovibrio, Thiobacillus, Arthrobacter, Flavobacterium, Beijerinckia, Rhizobium, Acinetobacter and Sulfolobus. Some of these microorganisms may have potential for degrading refractory organic sulfur compounds as discussed by Hedrick et al, (Hedrick, et al., 1982), "Desulfurization of Coal by Biological Pretreatment," State-of-the-art. A comprehensive summary of the experimental work in this area is presented in this report. Neither this report nor other available art discloses the mutant microorganisms Acinetobacter species CB2 (ATCC #53515) or its efficacy in removing organic sulfur from such as the aromatic sulfides found in carbonaceous materials.

An especially advantageous Pseudomonas species known as CB1 is described in U.S. Pat. No. 4,562,156 issued on the Dec. 31, 1985.

Although CB1 activity oxidizes certain types of organic sulfur, it does not have sufficient activity for oxidation of certain other types of organic sulfur.

SUMMARY OF THE INVENTION

Acinetobacter species CB2 (ATTC #53515) hereinafter referred to simply as "CB2," is a nonmotile, short, plump, gram negative rod approximately 1×2 um in logarithmic phase, nearly coccus shape in stationary phase, present predominantly in pairs and short chains. Filaments and large irregular cells have been observed. This microorganism is oxidase negative, catalase positive. Optimum pH for growth is near neutral (pH 7.0) at temperatures ranging from 30°-35° C. Acinetobacter species CB2 is an aerobic organism which is sensitive to ampicillin.

CB2 is capable of using citrate as a carbon source and is lactose negative on MacConkey's agar. Small yellow-green colonies are formed on Trypticase soy agar. Colonies formed on nutrient agar are green-yellow and translucent. CB2 does not use phenol or naphthalene as a sole source of carbon for growth and energy but is able to use resorcinol as a sole carbon source.

A culture of CB2 was deposited in the internationally known and accepted American Type Culture Collection (ATTC), 12301 Parklawn Drive, Rockville, MD 20852, U.S.A. in viable and reproductive condition on the July 15, 1986 under the provisions of the Budapest Treaty. The ATTC has assigned ATCC #53515 to CB2.

The organism was developed from a mixed microbial population isolated from soil obtained at a coal mine in the state of Pennsylvania in the United States of America. Microorganisms in this mixed microbial population were treated with a nutagen, "rescued", adapted for use of resorcinol as a carbon source and selected for microorganisms capable of oxidizing diphenyl sulfide (DPS) in aqueous medium.

The mutant microorganism, CB2, successfully oxidizes the aromatic sulfur found in DPS to sulfate and is useful in oxidizing and removing this sulfur form from carbonaceous substrates without utilization of the carbonaceous material.

Microbial cultures successfully adapted to and selected for growth on resorcinol in ethanol were tested for oxidation of DPS in aqueous medium by the following procedure. Microbial cultures were grown in minimal salts medium containing 1 ml of 10% resorcinol in ethanol on a shaking table at room temperature overnight. Each of the overnight cultures was inoculated with DPS at the same concentration. The DPS dosed microbial cultures and controls were returned to the shaking table and incubated overnight under ambient conditions. To determine the amount of DPS remaining in the aqueous medium, the entire contents of each flask were extracted with methylene chloride. The solvent extract from each flask was measured and brought to a constant 50 ml volume with methylene chloride prior to analysis by gas chromatography using a flame ionization detector.

One of the resulting cultures, arbitrarily named "R-Coal-E," demonstrated significant reduction in DPS. Following confirmation of the DPS reduction in aqueous medium, the culture was streaked onto nutrient agar for isolation. Two colonial forms were observed on nutrient agar: a medium-small, round, translucent yellow-green colony and a very small, off-white translucent colonial form. Each of these colony types was isolated onto separate nutrient agar plates. Single colony isolation was performed three times and from the third isolation a single colony was subcultured into nutrient broth and subsequently into minimal salts medium plus resorcinol in ethanol. The medium-small colonial form grew well in the minimal salts resorcinol broth. The small, translucent off-white colonial type was unable to use resorcinol in ethanol as a carbon source. The parent culture, "R-Coal-E" (containing two colonial forms) and the medium-small colonial isolate were compared for activity with respect to DPS. The single colony isolate, arbitrarily named "R-Coal E-1", was designated CB2 and identified as an Acinetobacter species.

EXAMPLE 1

This example relates to plasmid analysis.

A variety of chemical agents such as acridine orange, as well as growth at elevated temperatures are able to free or "cure" some bacterial cells of plasmid DNA molecules. Plasmids which exist as autonomously replicating circular DNA duplexes are eliminated by these agents either because of interference with replication (Acridines) or by alteration of their membrane attachment sites (elevated temperatures).

The curing procedure used with CB2 was performed in accordance with the one disclosed in the "Manual of Methods for General Bacteriology" (Gerhardt, P. 1981), Manual of Methods for General Bacteriology, American Society for Microbiology, Washington, DC, USA. The CB2 culture in the logarithmic growth phase was inoculated at $10^3$ to $10^4$ cells into a series of tubes containing nutrient broth with 50 or 250 mg/L acridine orange. Cultures were incubated overnight with aeration at 25° C. or at 40° C. A portion of each culture was then diluted 1:100 into fresh medium and allowed to grow at 25° C. or 40° C. with no aeration. Appropriate dilutions of the culture were placed on nutrient agar to obtain single colonies. Single colony isolates were tested for DPS oxidation.

Stock cultures of CB2, and acridine orange treated single colony isolates (isolate #7 and isolate #17) which showed decreased DPS oxidation were streaked onto nutrient agar plates and submitted for isolation of plasmid DNA using the methods of Birnboim and Doly (Birnboim, H. C. and Doly, J., "A Rapid Alkaline Extraction Procedure for Screening Recombinant Plasmid DNA," Nucleic Acids Research, 7: 1513–1523) and Lysis in the Well" Techniques of Newland et al., (1980) "Rapid Screening for Plasmids in Environmental Isolates of *Vibrio cholerae* by an "in the wall" Lysis Technique Using Horizontal Gel Electrophoresis, Abstracts Proc., 3rd Annual Mid-Atlantic Regional Extrachromosomal Elements Meeting, *Plasmid*, 3: 238).

These plasmid analytic procedures demonstrated that CB2, not treated for plasmid removal contained a small plasmid. A small plasmid was detected in isolate #17. No plasmids were detected in isolate #7. Isolates #17 and #7 exhibited decreased activity with respect to DPS following acridine orange treatment. The loss of activity with respect to DPS does not appear to be the result of plasmid loss because both isolate #17 with a small plasmid similar in size to the one found in CB2 and isolate #7 demonstrated decreased activity on DPS. If the activity were plasmid mediated, the small plasmid present in isolate #17 would likely produce the enzymes needed for oxidation of DPS.

From this example it is reasonable to conclude that the oxidation of DPS is due to chromosomal DNA and not to plasmid DNA.

EXAMPLES 2–38

These examples constitute a large number of tests conducted in order to determine the biochemical characteristics of CB2.

Biochemical characterization of CB2, and the most closely related microorganism, *Acinetobacter calcoaceticus var lwoffi*, were performed using the API 20E System (API 20E System Analytical Profile Index, Analab Products, Plainview, NY). Profiles for CB2 and the closely related Acinetobacter species are presented in Table 1.

TABLE 1

| | | COMPARATIVE TESTS | |
|---|---|---|---|
| Example | API Test | CB2 | *Calcoaceticus var lwoffi* |
| 2 | ONPG | − | − |
| 3 | ADH | − | − |
| 4 | LDC | − | − |
| 5 | ODC | − | − |
| 6 | CIT | + | − |
| 7 | H₂S | − | − |
| 8 | URE | − | − |
| 9 | TDA | − | − |
| 10 | IND | − | − |
| 11 | VP | − | − |
| 12 | GEL | + | − |
| 13 | GLU | − | − |
| 14 | MAN | − | − |
| 15 | INO | − | − |
| 16 | SOR | − | − |
| 17 | RHA | − | − |
| 18 | SAC | − | − |
| 19 | MEL | − | − |
| 20 | AMY | − | − |
| 21 | ARA | − | − |
| 22 | OXI | − | − |
| 23 | NO | − | − |
| 24 | N GAS | + | − |
| 25 | MOTILITY | − | − |
| 26 | MAC | + | − |
| 27 | OF-O | − | − |
| 28 | OF-F | − | − |
| 29 | 41° C. | − | + |
| 30 | PHENOL | − | − |
| 31 | NAPHTHALENE | − | − |
| 32 | RESORCINOL | + | − |
| 33 | TSA | Small, green-yellow colonies | Large, off-white colonies growth slow |
| 34 | NA | Green-yellow translucent colonies, dry | Off-white, sticky, translucent colonies |
| 35 | MAC | Translucent colonies slight yellowing of the plate | No growth |
| 36 | GRAM STAIN | Gram-, small coccobacilli, single, pairs, chains | Gram-, small coccobacilli, mostly in pairs |
| 37 | AMPICILLIN | Sensitive | Sensitive |
| 38 | CATALASE | + | + |

A complete description of the manner in which the tests listed in Column 2 of Table 1 are conducted is given in the publication entitled "API 20E System" published in October of 1984 by Sherwood Medical Incorporated, 200 Express Street, Plainview, N.Y., 11803 USA.

In Columns 3 and 4 of Table 1 a plus sign (+) indicates that the corresponding test was positive whereas a negative sign (−) indicates that the test was negative.

As can been seen in Table 1 the large number of tests as to which identical results are given tends to prove that CB2 is a species of Acinetobacter. On the other hand, those tests which give a different result tend to prove that CB2 is a novel species.

EXAMPLE 39

This example relates to mechanistic studies with DPS.

Overnight cultures of CB2 were inoculated with 200 mg/L DPS and allowed to incubate on a shaking table at room temperature overnight. One of the DPS treated flasks was extracted with methylene chloride and the extract analyzed by GC/FID for DPS and compared to the methylene chloride extract of a control medium inoculated with 200 mg/L DPS. This analysis indicated that the solvent extractable DPS had been reduced by 83% when compared to the control value for DPS. The contents of the second flask were centrifuged to remove the biomass and filtered prior to analysis for sulfate. The sulfate analysis was carried out as described in the Hach Handbook for Water Analysis (Hach Chemical Company, 1979). Analysis of a control flask in which CB2 was grown overnight in minimal salts with resorcinol in ethanol gave a sulfate concentration of 45 mg/L. Analysis of the filtrate from the CB2/minimal salts and resorcinol/ethanol/DPS treatment flask gave a sulfate concentration of 125 mg/L. The observed increase of 71 ppm in sulfate in the DPS treated flask corresponds well with the theoretical increase of 85.6 mg/L sulfate by oxidation of 83% of the 200 mg/L DPS by CB2.

This examples proves that oxidation of DPS by CB2 results in liberation of the sulfur in the form of water soluble sulfate.

EXAMPLE 40

This example proves that CB2 acts on organic sulfur in coal.

Organic sulfur in coal is determined by an indirect method which involves analysis for pyritic sulfur, sulfate sulfur and total sulfur. The organic sulfur is determined by the difference between the total sulfur and the sum of the pyritic sulfur and sulfate sulfur. To demonstrate that CB2 acts on organic sulfur in coal, the coal to be treated was washed to remove the sulfate sulfur. The washed coal was treated with CB2 and total sulfur reductions of as much as 13% were observed. CB2 was grown in minimal salts medium containing resorcinol in ethanol overnight and subsequently incubated with 0.2 g iron pyrite. A control flask contained only salts, resorcinol in ethanol and iron pyrite, no microorganisms. The flasks were allowed to incubate on a shaking table at room temperature and pH of 7±0.2. The contents of each flask were centrifuged following the incubation. The pyrite/biomass harvested from the centrifugation was washed twice with distilled water and was dried at 60° C. overnight and analyzed for total sulfur content using a Fisher total sulfur analyzer. The total sulfur contents of the control and experimental pyrite (treated with CB2) were identical.

These results indicate that CB2 does not oxidize iron pyrite. Thus, following removal of water soluble sulfates from coal, CB2 removed significant amounts of sulfur and was shown to have no activity in oxidation of pyritic sulfur. These findings indicate that organic sulfur is the target for activity of CB2.

EXAMPLE 41

This example compares the oxidation of DPS in aqueous medium by the parent microbial culture (dual culture, R-Coal-E) and the mutant microorganism CB2.

The results of these experiments are presented in Table 2. DPS was spiked into each culture and control at 200 mg/L.

TABLE 2

| COMPARISON OF DPS OXIDATION BY "R-COAL-E" AND BY CB2 | |
|---|---|
| % Reduction in Solvent Extractable DPS | |
| R-Coal-E Treatment | CB2 Treatment |
| 87 | 92 |
| 60 | 64 |
| 70 | 81 |
| 82 | 74 |
| 67 | 65 |
| 88 | 79 |

By reference to Table 2 it can been seen that oxidation of DPS by the mixed microbial culture called "R-Coal-E" and by CB2, single colony isolate, are equivalent. Therefore, the activity with respect to DPS is the result of oxidation of DPS by CB2.

EXAMPLES 42-50

The examples compare the effectiveness of CB2 with two other known species with regard to the ability of cultures of all three to oxidize diphenyl sulfide (DPS).

Oxidation of DPS at 200 mg/L in aqueous medium by CB2, *Acinetobacter lwoffi* (the ATCC microbial culture most closely related to CB2 biochemically) and a mutant microorganism, CB1, developed to oxidize thiophenic sulfur. Results from these experiments are presented in Table 3.

TABLE 3

| DPS OXIDATION BY CB2, CB1 AND *ACINETOBACTER LWOFFI* | | | |
|---|---|---|---|
| Example (No) | Inventive (I)/ Comparative (C) | Microbial Culture | Decrease in Solvent Extractable DPS (%) |
| 42 | I | CB2 | 83 |
| 43 | I | CB2 | 81 |
| 44 | I | CB2 | 84 |
| 45 | I | CB2 | 75 |
| | | | 81 Average |
| 46 | C | CB1 | 22 |
| 47 | C | CB1 | 18 |
| | | | 20 Average |
| 48 | C | Acinetobacter lwoffi | 18 |
| 49 | C | Acinetobacter lwoffi | 32 |
| 50 | C | Acinetobacter lwoffi | 10 |
| | | | 20 Average |

By reference to Table 3 it can be seen that the novel microbe, CB2, decreases solvent extractable DPS by 81%. On the other hand the previously known Pseudomonas species, CB1 descreases solvent extractability of DPS by only 20%. Thus, CB2 is four times as effective as is CB1.

Similarly *Acinetobacter lwoffi*, another known species, decreases solvent extractable DPS by only 20%. CB2 is therefore, four times as effective as is *Acinetobacter lwoffi*.

EXAMPLES 51-69

These examples were conducted to evaluate the ability of the mutant microbe, CB2, to remove sulfur from different coals.

CB2 cultures were inoculated into minimal salts medium containing resorcinol in ethanol for overnight growth on a shaking table at room temperature (25° C.). Powdered coal (−60 mesh or smaller) was added to each 18-24 hour microbial culture at 10 grams per 100 ml. Flasks containing the microbial culture/coal mixture were placed on the shaking table and incubated for 18-24 hours prior to harvesting of the coal by centrifugation, washing of the coal pellet with distilled water and analysis of the coal for total sulfur. Total sulfur analyses were performed on untreated dried coal from each coal sample, on coal samples washed with the minimal salts medium (no microbes) and on coal samples treated with CB2. Data in Table 4 illustrate total sulfur removal and estimates organic sulfur removal from several coals by treatment with CB2.

TABLE 4

| Example | Type of Coal | % Total Control (Washed) | Sulfur CB2 Treated | % Total Sulfur Reduction | % Organic Sulfur Reduction |
|---|---|---|---|---|---|
| 51 | Kentucky #9 | 3.66* | 3.23 | 12 | 30 |
| 52 | | 3.66* | 3.25 | 11 | 28 |
| 53 | | 3.99 | 3.70 | 8 | 21 |
| | | | 3.69 | 8 | 21 |
| 54 | | 4.06 | 3.70 | 9 | 25 |
| 55 | | 4.00 | 3.54 | 11 | 32 |
| 56 | | 4.06 | 3.80 | 7 | 18 |
| 57 | | 3.94 | 3.50 | 11 | 31 |
| 58 | | 3.95 | 3.76 | 5 | 14 |
| 59 | Homer City | 2.06 | 1.80 | 13 | 33 |
| 60 | Upper Freeport | 2.00 | 1.79 | 11 | 26 |
| 61 | | 2.00 | 1.90 | 5 | 13 |
| 62 | | 2.10 | 1.87 | 11 | 29 |
| 63 | | 1.88 | 1.70 | 10 | 23 |
| 64 | | 2.10 | 1.87 | 11 | 29 |
| 65 | | 2.10 | 1.83 | 13 | 34 |
| 66 | Peabody | 3.30 | 3.10 | 6 | 15 |
| 67 | Illinois #6 | | 3.08 | 7 | 16 |
| 68 | Ohio #8 | 4.51 | 4.27 | 6 | 13 |
| 69 | | | 4.26 | 6 | 13 |

*Stored under ethanol prior to treatment.

By reference to Table 4 it can be seen that CB2 reduced both the total sulfur content and the organic sulfur content of every type of coal tested.

EXAMPLES 70-77

These examples were conducted to compare sulfur removal using the mutant microbe CB1 for removal of thiophenic sulfur, and the mutant microbe, CB2, for putative removal of aromatic sulfides from coal.

Microbial cultures were inoculated into minimal salts medium containing benzoate in the case of CB1 and resorcinol in the case of CB2 for growth on a shaking table under ambient conditions overnight. Powdered coal (−60 mesh or smaller) was added to each flask at the rate of 10 grams per 100 ml of solution, and the flasks containing the microbe/coal mixture and the medium/coal mixture were replaced on the shaking table for incubation overnight. The contents of each flask were harvested by centrifugation, washed with distilled water, dried at 60° C. and analyzed for total sulfur. Total sulfur analyses were performed on the washed coal control samples and on coal samples treated with CB1 or CB2. Additional experiments monitored the sulfur removal of CB1 and CB2 when the microbial cultures were used sequentially. Data presented on Table 5 illustrate sulfur removal by CB1, CB2 and both microorganisms.

TABLE 5

| Example | Type of Coal | Sample | % Total Sulfur |
|---|---|---|---|
| 70 | Illinois #6 | Control | 3.30 |
| 71 | Illinois #6 | CB1 | 2.90 |
| 72 | Illinois #6 | CB2 | 3.10 |
| 73 | Illinois #6 | CB1 then CB2 | 2.70 |
| 74 | Homer City | Control | 1.98 |
| 75 | Homer City | CB1 | 1.83 |
| 76 | Homer City | CB2 | 1.90 |
| 77 | Homer City | CB1 then CB2 | 1.75 |

By reference to Table 5 it can be seen that the sequential treatment of coal with CB1 followed by CB2 resulted in desulfurization equivalent to the sulfur removed by CB1 and the sulfur removed by CB2. This additive effect of sequential treatment shows that CB2 removes an organic sulfur form other than thiophenic sulfur which is removed by CB1.

Although the invention has been described in considerable detail with reference to certain preferred embodiments thereof, it will be understood that variations and modifications can be made within the spirit and scope of the invention as described above and as defined in the appended claims.

What is claimed is:

1. A biologically pure microorganism having all the identifying characteristics of Acinetobacter species CBS ATCC #53515.

2. A biologically pure culture of mutant Acinetobacter species CB2 ATCC #53515, mutants or variants thereof.

3. A process for removing organic sulfur compounds from a carbonaceous substrate comprising treating said substrate with a culture of Acinetobacter species CB2 ATCC #53515.

4. The process of claim 3 in which the substrate is coal.

5. The process of claim 3 in which the substrate is petroleum and/or products thereof.

* * * * *